(12) United States Patent
Watanabe et al.

(10) Patent No.: US 6,908,719 B1
(45) Date of Patent: Jun. 21, 2005

(54) PHOTOSENSITIVE COMPOUND AND PHOTOSENSITIVE COMPOSITION

(75) Inventors: Tetsuya Watanabe, Kyoto (JP); Takao Mukai, Kyoto (JP); Yasunori Niwa, Inazawa (JP); Keiko Noda, Inazawa (JP); Chiyoji Watanabe, Inazawa (JP)

(73) Assignees: Sanyo Chemical Industries, Ltd., Kyoto (JP); Sony Corporation, Tokyo (JP)

( * ) Notice: Subject to any disclaimer, the term of this patent is extended or adjusted under 35 U.S.C. 154(b) by 0 days.

(21) Appl. No.: 09/700,907
(22) PCT Filed: Mar. 31, 2000
(86) PCT No.: PCT/JP00/02063
§ 371 (c)(1), (2), (4) Date: Jan. 8, 2001
(87) PCT Pub. No.: WO00/58275
PCT Pub. Date: Oct. 5, 2000

(30) Foreign Application Priority Data
Mar. 31, 1999 (JP) .............................................. 1192635

(51) Int. Cl.$^7$ ............................. G03F 7/012; G03F 7/30
(52) U.S. Cl. .......................... 430/28; 430/167; 430/197; 552/8
(58) Field of Search ......................... 430/167, 28, 197; 552/8

(56) References Cited

U.S. PATENT DOCUMENTS

| | | | | |
|---|---|---|---|---|
| 2,848,328 A | * | 8/1958 | Hepher | 430/197 |
| 3,092,494 A | * | 6/1963 | Sus et al. | 430/168 |
| 3,598,586 A | | 8/1971 | Gaspar | |
| 4,160,698 A | | 7/1979 | Miyairi et al. | |
| 4,191,573 A | * | 3/1980 | Toyama et al. | 430/166 |
| 4,332,874 A | * | 6/1982 | Hayashi et al. | 430/28 |
| 4,469,778 A | | 9/1984 | Iwayanagi et al. | |
| 4,469,779 A | | 9/1984 | Suits | |
| 4,820,619 A | * | 4/1989 | Sanada et al. | 430/197 |
| 5,041,570 A | * | 8/1991 | Tochizawa et al. | 552/8 |
| 5,705,309 A | * | 1/1998 | West et al. | 430/167 |

OTHER PUBLICATIONS

Journal of Photochemistry and Photobiology, A: Chemistry, 87(1), 61–5 1995 (Ohana et al).*

* cited by examiner

Primary Examiner—John S. Chu
(74) Attorney, Agent, or Firm—Connolly Bove Lodge & Hutz LLP

(57) ABSTRACT

The present invention relates to a water-soluble photosensitive compound represented by the general formula (1):

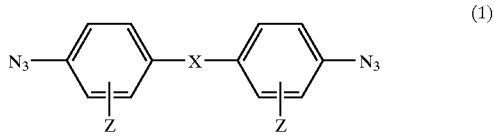

or by the general formula (2):

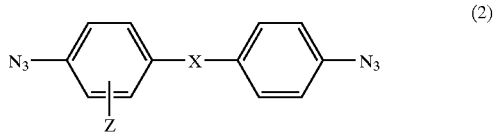

in the formula, X represents a direct bond, an alkylene group containing 1 to 5 carbon atoms, —CH$_2$O—, —OCH$_2$—, —CH$_2$OCH$_2$—, —O—, —S— or —SO$_2$—, and Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl, carbonyloxy or oxycarbonyl group, wherein a photosensitive group has an absorption maximum wavelength of not longer than 305 nm in the ultraviolet absorption spectrum thereof.

21 Claims, No Drawings

PHOTOSENSITIVE COMPOUND AND PHOTOSENSITIVE COMPOSITION

TECHNICAL FIELD

The present invention relates to a photosensitive compound and a photosensitive composition and, more particularly, it relates to a water-soluble photosensitive compound having an ultraviolet absorption maximum assignable to a photosensitive group in the short wavelength ultraviolet region and to a water-soluble photosensitive composition comprising said compound.

BACKGROUND ART

In the art, photosensitive compositions are used as materials for forming desired fine patterns by exposure to ultraviolet rays or like active energy beams.

As regards photosensitive compositions containing an azide compound, among others, Japanese Kokai Publication Sho-48-79970 discloses a photosensitive composition comprising polyvinylpyrrolidone and an azide compound and Japanese Kokai Publication Sho-50-33764 discloses a photosensitive composition comprising an acrylamide-diacetone acrylamide copolymer and an azide compound.

Stilbene-based azide compounds are used as the azide compounds in the above photosensitive compositions. The stilbene-based azides have an absorption maximum wavelength of 335 nm or longer, and the photosensitive compositions containing such azide compounds show satisfactory resolution upon close contact exposure but have a problem in that, upon proximity exposure, they cannot show satisfactory resolution. It has thus been earnestly desired that the resolution be improved.

DISCLOSURE OF INVENTION

As a result of intensive investigations made by the present inventors to solve such problem with the prior art photosensitive compositions, it was found that a water-soluble photosensitive composition containing a water-soluble photosensitive compound whose photosensitive group has an absorption maximum wavelength of 305 nm or shorter in the ultraviolet absorption spectrum thereof show very high resolution. Such finding has now led to completion of the present invention.

Thus, the present invention provides a water-soluble photosensitive compound represented by the following general formula (1):

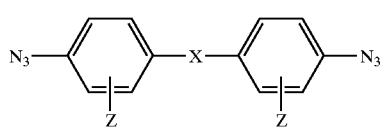

(1)

in the formula, X represents a direct bond, an alkylene group containing 1 to 5 carbon atoms, —CH$_2$O—, —OCH$_2$—, —CH$_2$OCH$_2$—, —O—, —S— or —SO$_2$—, Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl, carbonyloxy or oxycarbonyl group, and the two Z groups may be the same or different or by the following general formula (2):

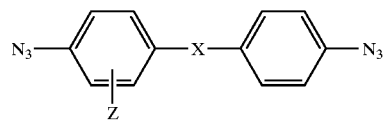

(2)

in the formula, X represents a direct bond, an alkylene group-containing 1 to 5 carbon atoms, —CH$_2$O—, —OCH$_2$—, —CH$_2$OCH$_2$—, —O—, —S— or —SO$_2$— and Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl, carbonyloxy or oxycarbonyl group, wherein a photosensitive group has an absorption maximum wavelength of not longer than 305 nm in the ultraviolet absorption spectrum thereof;

and a water-soluble photosensitive composition comprising 1 to 30% by mass of a water-soluble photosensitive compound (A) and 70 to 99% by mass of a water-soluble vinyl (co)polymer (B), wherein a photosensitive group in said (A) has an absorption maximum wavelength of not longer than 305 nm in the ultraviolet absorption spectrum thereof.

The C$_{1-5}$ alkylene group represented by X in the general formula (1) or (2) includes straight-chain alkyl groups such as methylene, ethylene, n-propylene, n-butylene, n-pentylene, etc.; and branched alkylene groups such as 1-methylethylene, 1-methylpropylene, 2-methylpropylene, 1-methylbutylene, 2-methylbutylene, 1,1-dimethylpropylene, 2,2-dimethylpropylene, etc.

Preferred as X in the general formula (1) or (2) are a direct bond, C$_{1-5}$ alkylene groups, —CH$_2$O—, —OCH$_2$—, —CH$_2$OCH$_2$—, —O—, —S— or —SO$_2$—. More preferred are a direct bond, methylene and ethylene.

In the general formula (1) or (2), Z is —SO$_3^-$.Q$^+$, —COO$^-$.Q$^+$ or —SO$_2$NR$_2$. Q$^+$ includes Li$^+$, Na$^+$, K$^+$ and N$^+$R, and, as R, there may be mentioned a hydrogen atom and/or C$_{1-5}$ alkyl groups such as methyl, ethyl, n- and i-propyl, n-, iso- and tert-butyl, n-pentyl, 2-methylbutyl and 3-methylbutyl; and C$_{1-5}$ alkyl groups having one hydroxy, ether, carbonyl, carbonyloxy or oxycarbonyl group, for example hydroxyalkyl groups such as hydroxymethyl, 2-hydroxyethyl, 3-hydroxypropyl, 2-hydroxypropyl, 3-hydroxy-1-methylpropyl, 4-hydroxybutyl and 5-hydroxypentyl; hydroxyalkoxyalkyl groups such as 2-(2-hydroxyethoxy)ethyl; alkoxyalkyl groups such as methoxymethyl, 2-methoxyethyl, 2-ethoxyethyl, 3-methoxypropyl, 3-ethoxypropyl, 3-propoxypropyl and 3-butoxybutyl; alkylcarbonyl(oxy)alkyl groups such as methylcarbonylmethyl, methylcarbonylethyl, methylcarbonylpropyl, methylcarbonyloxymethyl, methylcarbonyloxyethyl and methylcarbonyloxypropyl; alkoxycarbonylalkyl groups such as methyloxycarbonylmethyl, methyloxycarbonylethyl and methyLoxycarbonylpropyl; and so forth.

Among these, from the solubility viewpoint, preferred are —SO$_3^-$.Q$^+$ groups (in which Q$^+$ represents Li$^+$, Na$^+$, K$^+$ or N$^+$R$_4$ and R represents a hydrogen atom and/or a C$_{1-5}$ alkyl group which may optionally have one hydroxy, ether, carbonyl, carbonyloxy or oxycarbonyl group, and the plural R groups may be the same or different). Particularly preferred are —SO$_3^-$.Na$^+$, —SO$_3^-$.K$^+$ or —SO$_3^-$.NR$_4^+$.

The absorption maximum wavelength, in the ultraviolet absorption spectrum, of the photosensitive group in the water-soluble photosensitive compound of the invention as represented by the general formula (1) or (2) is generally not longer than 305 nm and, in cases where a high pressure mercury lamp or super-high pressure mercury lamp is used as the exposure light source, it is preferably 240 to 300 nm from the viewpoint of matching between exposure light intensity and resolution.

The "absorption maximum wavelength, in the ultraviolet absorption spectrum, of a photosensitive group" means the absorption maximum wavelength of a photosensitive functional group [e.g. the azide group in the general formula (1) or (2)] and no consideration is given to the absorption maximum wavelength(s) of a nonphotosensitive functional group(s).

Preferred among the photosensitive compounds of the present invention as represented by the general formula (1) or (2) from resolution, sensitivity and solubility viewpoints are disodium 4,4'-diazido-2,2'-biphenylenedisulfonate, disodium 4,4'-diazido-3,3'-biphenylenedisulfonate, disodium 4,4'-diazido-2,2'-methylenedibenzenedisulfonate, disodium 4,4'-diazido-3,3'-methylenedibenzenedisulfonate, disodium 4,4'-diazido-2,2'-(1,2-ethanediyldibenzene)disulfonate and disodium 4,4'-diazido-3,3'-(1,2-ethanediyldibenzene)disulfonate.

The processes for producing the photosensitive compounds of the invention as represented by the general formula (1) or (2) are described in the following.

1. When Z in the general formula (1) is $-SO_3^-.Q^+$ ($Q^+$ being $Li^+$, $Na^+$ or $K^+$)

(1) When X in the general formula (1) is a direct bond:
A 2-nitrobenzenesulfonic acid derivative (e.g. sodium 2-nitrobenzenesulfonate) or a 3-nitrobenzenesulfonic acid derivative (e.g. sodium 3-nitrobenzenesulfonate) is treated with zinc dust in the presence of an alkali (e.g. sodium hydroxide) and the resulting hydrazobenzene derivative is treated with sulfuric acid to give the corresponding 4,4'-diaminobiphenyl derivative. This is diazotized using sodium nitrite under acidic conditions in the presence of hydrochloric acid, followed by reaction with sodium azide, to give the desired product.

(2) When X in the general formula (1) is a methylene group:
An 2-anilinesulfonic acid derivative (e.g. sodium 2-anilinesulfonate) or an 3-anilinesulfonic acid derivative (e.g. sodium 3-anilinesulfonate) is treated with formalin under acidic conditions to give the corresponding 4,4'-diaminodiphenylmethane derivative. This is diazotized using sodium nitrite under acidic conditions in the presence of hydrochloric acid, followed by reaction with sodium azide, to give the desired product.

(3) When X in the general formula (1) is an alkylene group containing 2 to 5 carbon atoms:
A 2-nitrobenzenesulfonic acid derivative (e.g. sodium 2-nitrobenzenesulfonate) or a 3-nitrobenzenesulfonic acid derivative. (e.g. sodium 3-nitrobenzenesulfonate) is treated with a $C_{2-5}$ α, ω-dichloroalkylene in the presence of aluminum chloride, followed by hydrogenation using palladium-carbon, to give the corresponding 4,4'-diaminodiphenyl-$C_{2-5}$-alkylene derivative. This is diazotized using sodium nitrite under acidic conditions in the presence of hydrochloric acid, followed by reaction with sodium azide, to give the desired product.

(4) When X in the general formula (1) is $-CH_2O-$ or $-OCH_2-$:
A 5-chloromethyl-2-nitrobenzenesulfonic acid derivative (e.g. sodium 5-chloromethyl-2-nitrobenzenesulfonate) or a 2-chloromethyl-5-nitrobenzenesulfonic acid derivative (e.g. sodium 2-chloromethyl-5-nitrobenzenesulfonate) is reacted with a 5-hydroxy-2-nitrobenzenesulfonic acid derivative or a 2-hydroxy-5-nitrobenzenesulfonic acid derivative in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(5) When X in the general formula (1) is $-CH_2OCH_2-$:
A 5-chloromethyl-2-nitrobenzenesulfonic acid derivative (e.g. sodium 5-chloromethyl-2-nitrobenzenesulfonate) or a 2-chloromethyl-5-nitrobenzenesulfonic acid derivative (e.g. sodium 2-chloromethyl-5-nitrobenzenesulfonate) is reacted with a 5-hydroxymethyl-2-nitrobenzenesulfonic acid derivative or a 2-hydroxymethyl-5-nitrobenzenesulfonic acid derivative in the presence of an alkali (e.g. sodium hydroxide), followed by hydrogenation using palladium-carbon, to give the corresponding 4,4'-diaminodibenzyl ether derivative. This is diazotized using sodium nitrite under acidic conditions in the presence of hydrochloric acid, followed by reaction with sodium azide, to give the desired product.

(6) When X in the general formula (1) is $-O-$:
A 5-hydroxy-2-nitrobenzenesulfonic acid derivative (e.g. sodium 5-hydroxy-2-nitrobenzenesulfonate) or a 2-hydroxy-5-nitrobenzenesulfonic acid derivative (e.g. sodium 2-hydroxy-5-nitrobenzenesulfonate) is reacted with a 5-chloro-2-nitrobenzenesulfonic acid derivative or a 2-chloro-5-nitrobenzenesulfonic acid derivative in the presence of an alkali (e.g. sodium hydroxide), followed by hydrogenation using palladium-carbon, to give the corresponding 4,4'-diaminodiphenyl ether derivative. This is diazotized using sodium nitrite under acidic conditions in the presence of hydrochloric acid, followed by reaction with sodium azide, to give the desired product.

(7) When X in the general formula (1) is $-S-$:
Phenyl sulfide is nitrated using nitric acid and sulfuric acid and then sulfonated using oleum, further followed by hydrogenation using palladium carbon, to give a 4,4'-diaminodiphenyl sulfide derivative. This is diazotized using sodium nitrite under acidic conditions in the presence of hydrochloric acid, followed by reaction with sodium azide, to give the desired product.

(8) When X in the general formula (1) is $-SO_2-$:
Phenyl sulfide is oxidized using m-chloroperbenzoic acid, then nitrated using nitric acid and sulfuric acid, and sulfonated using oleum, further followed by hydrogenation using palladium-carbon, to give a 4,4'-diaminodiphenyl sulfone derivative. This is diazotized using sodium nitrite under acidic conditions in the presence of hydrochloric acid, followed by reaction with sodium azide, to give the desired product.

2. When Z in the general formula (1) is $-SO_3^-.Q^+$ ($Q^+$ being $N^+R_4$)
Those compounds in which Z is $-SO_3^-.Q(Q^+$ being $Li^+$, $Na^+$ or $K^+$) as obtained as mentioned above under 1. are acidified with hydrochloric acid and then reacted with $HO^-.N^+R_4$, to give the desired products.

3. When Z in the general formula (1) is $-COO^-.Q^+$ ($Q^+$ being $Li^+$, $Na^+$ or $K^+$)

(1) When X in the general formula (1) is a direct bond:
A 2-nitrobenzoic acid derivative (e.g. sodium 2-nitrobenzoate) or a 3-nitrobenzoic acid derivative (e.g. sodium 3-nitrobenzoate) is treated with zinc dust in the presence of an alkali (e.g. sodium hydroxide), and the resulting hydrazobenzene derivative is treated with sulfuric acid to give the corresponding 4,4'-diaminobiphenyl derivative. This is diazotized using sodium nitrite under acidic conditions in the presence of hydrochloric acid, followed by reaction with sodium azide, to give the desired product.

(2) When X in the general formula (1) is a methylene group:

An 2-anilinecarboxylic acid derivative (e.g. sodium 2-anilinecarboxylate) or an 3-anilinecarboxylic acid derivative (e.g. sodium 3-anilinecarboxylate) is treated with formalin under acidic conditions to give the corresponding 4,4'-diaminodiphenylmethane derivative. This is diazotized using sodium nitrite under acidic conditions in the presence of hydrochloric acid, followed by reaction with sodium azide, to give the desired product.

(3) When X in the general formula (1) is an alkylene group containing 2 to 5 carbon atoms:

A 2-nitrobenzoic acid derivative (e.g. sodium 2-nitrobenzoate) or a 3-nitrobenzoic acid derivative (e.g. sodium 3-nitrobenzoate) is treated with a $C_{2-5}$ α, ω-dichloroalkylene in the presence of aluminum chloride, followed by hydrogenation using palladium-carbon, to give the corresponding 4,4'-diaminodiphenyl-$C_{2-5}$-aklyene derivative. This is diazotized using sodium nitrite under acidic conditions in the presence of hydrochloric acid, followed by reaction with sodium azide, to give the desired product.

(4) When X in the general formula (1) is —$CH_2O$— or —$OCH_2$—:

A 5-chloromethyl-2-nitrobenzoic acid derivative (e.g. sodium 5-chloromethyl-2-nitrobenzoate) or a 2-chloromethyl-5-nitrobenzoic acid derivative (e.g. sodium 2-chloromethyl-5-nitrobenzenoate) is reacted with a 5-hydroxy-2-nitrobenzoic acid derivative or a 2-hydroxy-5-nitrobenzoic acid derivative in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(5) When X in the general formula (1) is —$CH_2OCH_2$—:

A 5-chloromethyl-2-nitrobenzoic acid derivative (e.g. sodium 5-chloromethyl-2-nitrobenzenoate or a 2-chloromethyl-5-nitrobenzoic acid derivative (e.g. sodium 2-chloromethyl-5-nitrobenzoate) is reacted with a 5-hydroxymethyl-2-nitrobenzoic acid derivative or a 2-hydroxymethyl-5-nitrobenzoic acid derivative in the presence of an alkali (e.g. sodium hydroxide), followed by hydrogenation using palladium-carbon, to give the corresponding 4,4'-diaminodibenzyl ether derivative. This is diazotized using sodium nitrite under acidic conditions in the presence of hydrochloric acid, followed by reaction with sodium azide, to give the desired product.

(6) When X in the general formula (1) is —O—:

A 5-hydroxy-2-nitrobenzoic acid derivative (e.g. sodium 5-hydroxy-2-nitrobenzoate) or a 2-hydroxy-5-nitrobenzenesulfonic acid derivative (e.g. sodium 2-hydroxy-5-nitrobenzoate) is reacted with a 5 chloro-2-nitrobenzoic acid derivative or a 2-chloro-5-nitrobenzoic acid derivative in the presence of an alkali (e.g. sodium hydroxide), followed by hydrogenation using palladium-carbon, to give the corresponding 4,4'-diaminodiphenyl ether derivative. This is diazotized using sodium nitrite under acidic conditions in the presence of hydrochloric acid, followed by reaction with sodium azide, to give the desired product.

(7) When X in the general formula (1) is —S—:

Phenyl sulfide is dibrominated using bromine and then carboxylated using carbon monoxide and a palladium catalyst. After subsequent nitration using nitric acid and sulfuric acid, hydrogenation is effected using palladium-carbon, to give a 4,4'-diaminodiphenyl sulfide derivative. This is diazotized using sodium nitrite under acidic conditions in the presence of hydrochloric acid, followed by reaction with sodium azide, to give the desired product.

(8) When X in the general formula (1) is —$SO_2$—:

Phenyl sulfide is oxidized with m-chloroperbenzoic acid, then dibrominated using bromine, and carboxylated using carbon monoxide and a palladium catalyst. After subsequent nitration using nitric acid and sulfuric acid, hydrogenation is effected using palladium-carbon, to give a 4,4'-diaminodiphenyl sulfone derivative. This is diazotized using sodium nitrite under acidic conditions in the presence of hydrochloric acid, followed by reaction with sodium azide, to give the desired product.

4. When Z in the general formula (1) is —$COO^-.Q^+$ ($Q^+$ being $N^+R_4$)

Those compounds in which Z is —$COO^-.Q^+$ ($Q^+$ being $Li^+$, $Na^+$ or $K^+$) as obtained as mentioned above under 3. are acidified with hydrochloric acid and then reacted with $HO^-.N^+R_4$, to give the desired products.

5. When Z in the general formula (1) is —$SO_2NR_2$

Those compounds in which Z is —$SO_3^-.Q^+$ as obtained as mentioned above under 1. are reacted with phosphorus pentachloride and then reacted with $R_2NH$ in the presence of a tertiary amine (e.g. pyridine) to give the desired products.

6. When Z in general formula (2) is —$SO_3^-.Q^+$ ($Q^+$ being $Li^+$, $Na^+$ or $K^+$)

(1) When X in general formula (2) is a direct bond:

A 2-nitrobenzenesulfonic acid derivative (e.g. sodium 2-nitrobenzenesulfonate) or a 3-nitrobenzenesuflonic acid derivative (e.g. sodium 3-nitrobenzenesulfonate) and nitrobenzene are treated with zinc dust in the presence of an alkali (e.g. sodium hydroxide) and the resulting hydrazobenzene derivative is treated with sulfuric acid, to give the corresponding 4,4'-diaminobiphenyl derivative. This is diazotized using sodium nitrite under acidic conditions in the presence of hydrochloric acid, followed by reaction with sodium azide, to give the desired product.

(2) When X in general formula (2) is a methylene group:

An 2-anilinesulfonic acid derivative (e.g. sodium 2-anilinesulfonate) or an 3-anilinesulfonic acid derivative (e.g. sodium 3-anilinesulfonate) and aniline are treated with formalin under acidic conditions, to give the corresponding 4,4'-diaminodiphenylmethane derivative. This is diazotized using sodium nitrite under acidic conditions in the presence of hydrochloric acid, followed by reaction with sodium azide, to give the desired product.

(3) When X in general formula (2) is an alkylene group containing 2 to 5 carbon atoms:

A 2-nitrobenzenesulfonic acid derivative (e.g. sodium 2-nitrobenzenesulfonate) or a 3-nitrobenzenesulfonic acid derivative (e.g. sodium 3-nitrobenzenesulfonate) and nitrobenzene are treated with a $C_{2-5}$ α, ω-dichloroalkylene in the presence of aluminum chloride, followed by hydrogenation using palladium-carbon, to give the corresponding 4,4'-diaminodiphenyl-$C_{2-5}$-alkylene derivative. This is diazotized using sodium nitrite under acidic conditions in the presence of hydrochloric acid, followed by reaction with sodium azide, to give the desired product.

(4) When X in general formula (2) is —$CH_2O$—:

A 5-chloromethyl-2-nitrobenzenesulfonic acid derivative (e.g. sodium 5-chloromethyl-2-nitrobenzenesulfonate) or a 2-chloromethyl-5-nitrobenzenesulfonic acid derivative (e.g. sodium 2-chloromethyl-5-nitrobenzenesulfonate) is reacted with 4-nitrophenol in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(5) When X in general formula (2) is OCH$_2$—:

4-Hydroxymethyl-nitrobenzene is reacted with a 5-chloro-2-nitrobenzenesulfonic acid derivative (e.g. sodium 5-chloro-2-nitrobenzenesulfonate) or a 2-chloro-5-nitrobenzenesulfonic acid derivative (e.g. sodium 2-chloro-5-nitrobenzenesulfonate) in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(6) When X in general formula (2) is —CH$_2$OCH$_2$—:

A 5-chloromethyl-2-nitrobenzenesulfonic acid derivative (e.g. sodium 5-chloromethyl-2-nitrobenzenesulfonate) or a 2-chloromethyl-5-nitrobenzenesulfonic acid derivative (e.g. sodium 2-chloromethyl-5-nitrobenzenesulfonate) is reacted with 4-hydroxymethylnitrobenzene in the presence of an alkali (e.g. sodium hydroxide), followed by hydrogenation using palladium-carbon, to give the corresponding 4,4'-diaminodibenzyl ether derivative. This is diazotized using sodium nitrite under acidic conditions in the presence of hydrochloric acid, followed by reaction with sodium azide, to give the desired product.

(7) When X in general formula (2) is —O—:

A 5-hydroxy-2-nitrobenzenesulfonic acid derivative (e.g. sodium 5-hydroxy-2-nitrobenzenesulfonate) or a 2-hydroxy-5-nitrobenzenesulfonic acid derivative (e.g. sodium 2-hydroxy-5-nitrobenzenesulfonate) is reacted with 4-chloronitrobenzene in the presence of an alkali (e.g. sodium hydroxide), followed by hydrogenation using palladium-carbon, to give the corresponding 4,4'-diaminodiphenyl ether derivative. This is diazotized using sodium nitrite under acidic conditions in the presence of hydrochloric acid, followed by reaction with sodium azide, to give the desired product.

(8) When X in general formula (2) is —S—:

Phenyl sulfide is nitrated using nitric acid and sulfuric acid and then monosulfonated using oleum, further followed by hydrogenation using palladium-carbon, to give a 4,4'-diaminodiphenyl sulfide derivative. This is diazotized using sodium nitrite under acidic conditions in the presence of hydrochloric acid, followed by reaction with sodium azide, to give the desired product.

(9) When X in general formula (2) is —SO$_2$—:

Phenyl sulfide is oxidized using m-chloroperbenzoic acid, then nitrated using nitric acid and sulfuric acid and monosulfonated using oleum, further followed by hydrogenation using palladium-carbon, to give a 4,4'-diaminodiphenyl sulfone derivative. This is diazotized using sodium nitrite under acidic conditions in the presence of hydrochloric acid, followed by reaction with sodium azide, to give the desired product.

7. When Z in general formula (2) is —SO$_3^-$.Q$^+$ (Q$^+$ being N$^+$R$_4$)

These compounds in which Z is —SO$_3^-$.Q$^+$ (Q$^+$ being Li+, Na$^+$ or K$^+$) as obtained as described above under 6. are rendered acidic using hydrochloric acid and then reacted with HO$^-$.N$^+$R$_4$ to give the desired compounds.

8. When Z in general formula (2) is —COO$^-$.Q$^+$ (Q$^+$ being Li$^+$, Na$^+$ or K$^+$)

(1) When X in general formula (2) is a direct bond:

A 2-nitrobenzoic acid derivative (e.g. sodium 2-nitrobenzoate) or a 3-nitrobenzoic acid derivative (e.g. sodium 3-nitrobenzoate) and nitrobenzene are treated with zinc dust in the presence of an alkali (e.g. sodium hydroxide) and the resulting hydrazobenzene derivative is treated with sulfuric acid, to give the corresponding 4,4'-diaminobiphenyl derivative. This is diazotized using sodium nitrite under acidic conditions in the presence of hydrochloric acid, followed by reaction with sodium azide, to give the desired product.

(2) When X in general formula (2) is a methylene group:

An 2-anilinecarboxylic acid derivative (e.g. sodium 2-anilinecarboxylate) or an 3-anilinecarboxylic acid derivative (e.g. sodium 3-anilinecarboxylate) and aniline are treated with formalin under acidic conditions to give the corresponding 4,4'-diaminodiphenylmethane derivative. This is diazotized using sodium nitrite under acidic conditions in the presence of hydrochloric acid, followed by reaction with sodium azide, to give the desired product.

(3) When X in general formula (2) is an alkylene group containing 2 to 5 carbon atoms:

A 2-nitrobenzoic acid derivative (e.g. sodium 2-nitrobenzoate) or a 3-nitrobenzoic acid derivative (e.g. sodium 3-nitrobenzoate) and nitrobenzene are treated with a C$_{2-5}$ α, ω-dichloroalkylene in the presence of aluminum chloride, followed by hydrogenation using palladium-carbon, to give the corresponding 4,4'-diaminodiphenyl-C$_{2-5}$-alkylene derivative. This is diazotized using sodium nitrite under acidic conditions in the presence of hydrochloric acid, followed by reaction with sodium azide, to give the desired product.

(4) When X in general formula (2) is —CH$_2$O—:

A 5-chloromethyl-2-nitrobenzoic acid derivative (e.g. sodium 5-chloromethyl-2-nitrobenzoate) or a 2-chloromethyl-5-nitrobenzoic acid derivative (e.g. sodium 2-chloromethyl-5-nitrobenzoate) is reacted with 4-nitrophenol in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(5) When X in general formula (2) is —OCH$_2$—:

4-Hydroxymethyl-nitrobenzene is reacted with a 5 chloro-2-nitrobenzoic acid derivative (e.g. sodium 5-chloro-2-nitrobenzoate) or a 2-chloro-5-nitrobenzoic acid derivative (e.g. sodium 2-chloro-5-nitrobenzoate) in the presence of an alkali (e.g. sodium hydroxide), followed by hydrogenation using palladium-carbon, to give the corresponding 4,4'-diaminobenzyloxybenzene derivative. This is diazotized using sodium nitrite under acidic conditions in the presence of hydrochloric acid, followed by reaction with sodium azide, to give the desired product.

(6) When X in general formula (2) is —CH$_2$OCH$_2$—:

A 5-chloromethyl-2-nitrobenzoic acid derivative (e.g. sodium 5-chloromethyl-2-nitrobenzoate) or a 2-chloromethyl-5-nitrobenzoic acid derivative (e.g. sodium 2-chloromethyl-5-nitrobenzoate) is reacted with 4-hydroxymethylnitrobenzene in the presence of an alkali (e.g. sodium hydroxide), followed by hydrogenation using palladium-carbon, to give the corresponding 4,4'-diaminodibenzyl ether derivative. This is diazotized using sodium nitrite under acidic conditions in the presence of hydrochloric acid, followed by reaction with sodium azide, to give the desired product.

(7) When X in the general formula (2) is —O—:

A 5-hydroxy-2-nitrobenzoic acid derivative (e.g. sodium 5-hydroxy-2-nitrobenzoate) or a 2-hydroxy-5-nitrobenzoic acid derivative (e.g. sodium 2-hydroxy-5-nitrobenzoate) is reacted with 4-chloronitrobenzene in the presence of an alkali (e.g. sodium hydroxide), followed by hydrogenation using palladium-carbon, to give the corresponding 4,4'-diaminodiphenyl ether derivative. This is diazotized using sodium nitrite under acidic conditions in the presence of hydrochloric acid, followed by reaction with sodium azide, to give the desired product.

(8) When X in general formula (2) is —S—:

Phenyl sulfide is monobrominated using bromine and carboxylated using carbon monoxide and a palladium catalyst. The subsequent nitration is effected using nitric acid and sulfuric acid, followed by hydrogenation using palladium-carbon, to give a 4,4'-diaminodiphenyl sulfide derivative. This is diazotized using sodium nitrite under acidic conditions in the presence of hydrochloric acid, followed by reaction with sodium azide, to give the desired product.

(9) When X in general formula (2) is —$SO_2$—:

Phenyl sulfide is oxidized using m-chloroperbenzoic acid, then monobrominated using bromine, and carboxylated using carbon monoxide and a palladium catalyst. The subsequent nitration is effected using nitric acid and sulfuric acid, followed by hydrogenation using palladium-carbon, to give a 4,4'-diaminodiphenyl sulfone derivative. This is diazotized using sodium nitrite under acidic conditions in the presence of hydrochloric acid, followed by reaction with sodium azide, to give the desired product.

9. When Z in general formula (2) is —$COO^-.Q^+$ ($Q^+$ being $N^+R_4$)

Those compounds in which Z is —$COO^-.Q^+$ ($Q^+$ being $Li^+$, $Na^+$ or $K^+$) as obtained as described above under 8. are acidified with hydrochloric acid and then reacted with $HO^-.N^+R_4$ to give the desired compounds.

10. When Z in general formula (2) is —$SO_2NR_2$

Those compounds in which Z is —$SO_3^-.Q^+$ as obtained as described above under 6. are reacted with phosphorus pentachloride and then with $R_2NH$ in the presence of a tertiary amine (e.g. pyridine) to give the desired products.

The water-soluble photosensitive compounds of the invention as represented by the general formula (1) or (2) can be identified by ordinary analytical means, for example by elemental analysis, $^1$H-NMR, $^{13}$C-NMR, ultraviolet and/or infrared spectroscopy, and/or mass spectrometry.

The water-soluble photosensitive composition of the present invention comprises (A) a water-soluble photosensitive compound in which a photosensitive group has an absorption maximum wavelength of not longer than 305 nm in the ultraviolet absorption spectrum and (B) a water-soluble vinyl (co)polymer, if necessary together with another or other components. The water-soluble photosensitive compound (A) is not particularly restricted as long as it has an absorption maximum wavelength of not longer than 305 nm in the ultraviolet absorption spectrum of the photosensitive group thereof and is soluble in water. Thus, it includes, among others, water-soluble azide compounds, water-soluble diazo compounds and water-soluble photooxidation acid generators.

From the resolution viewpoint, water-soluble azide compounds are preferred and water-soluble azide compounds represented by the above general formula (1) or (2) are particularly preferred.

The above water-soluble photosensitive compound (A) has a photosensitive group showing an absorption maximum wavelength of not longer than 305 nm in the ultraviolet absorption spectrum, with shifting to the shorter wavelength side as compared with the absorption maximum wavelengths (e.g. 335 to 450 nm) of the so-far known stilbene-based azide compounds. Therefore, when pattern forming is carried out using a photosensitive composition containing (A) by ultraviolet exposure, the resolution can be still more improved as compared with photosensitive compositions containing a stilbene-derived azide compound.

The absorption maximum wavelength, in the ultraviolet absorption spectrum, of the photosensitive group(s) of the above water-soluble photosensitive compound (A) is generally not longer than 305 nm and, when the exposure light source is a high pressure mercury lamp or super-high pressure mercury lamp, it is preferably 240 to 300 nm from the viewpoint of matching between exposure light intensity and resolution.

The amount of (A) to be incorporated in the photosensitive composition of the invention is generally 1 to 30% by mass, preferably 1 to 20% by mass, based on the mass of the photosensitive composition, from the viewpoint of sensitivity and adhesion.

(A) may comprise a single species or a mixture of two or more species.

The water-soluble vinyl (co)polymer (B) to be used in the water-soluble photosensitive composition of the invention is not particularly restricted but includes, among others, N-vinylpyrrolidone (co)polymers, N-vinylformamide (co)polymers, N-vinylacetamide (co)polymers, (meth)acrylamide (co)polymers, N-$C_{1-5}$-alkyl(meth)acrylamide (co)polymers, N,N-di-$C_{1-5}$-alkyl(meth)acrylamide (co)polymers, (meth)acrylamide-diacetone (meth)acrylamide copolymers, acryloylmorpholine (co) polymers, acrylamide-2-methylpropanesulfonic acid (co)polymers, vinyl alcohol (co)polymers, sodium styrenesulfonate (co)polymers, (meth)acrylic acid (co)polymers, styrylpyridinium salt compounds described in Japanese Kokai Publication Sho-55-23163, casein, gelatin, methylcellulose, hydroxypropylcellulose, polyvinylcellulose and polyethylene glycol.

Preferred among them from the sensitivity viewpoint are N-vinylpyrrolidone (co) polymers, N-vinylformamide (co) polymers, N-vinylacetamide (co)polymers, (meth) acrylamide (co)polymers, N-$C_{1-5}$-alkyl(meth)acrylamide (co)polymers, N,N-di-$C_{1-5}$-alkyl(meth)acrylamide (co) polymers, (meth)acrylamide-diacetone (meth)acrylamide copolymers, acryloylmorpholine (co) polymers, acrylamide-2-methylpropanesulfonic acid (co)polymers, vinyl alcohol (co)polymers, sodium styrenesulfonate (co)polymers and (meth)acrylic acid (co)polymers, and, particularly preferred are N-vinylpyrrolidone (co)polymers, N-vinylformamide (co)polymers, N-vinylacetamide (co)polymers and (meth) acrylamide-diacetone(meth)acrylamide copolymers.

Considering the sensitivity and viscosity of the photosensitive composition, the above water-soluble vinyl (co) polymer (B) should generally have a weight average molecular weight (as determined by GPC) of 50,000 to 2,000,000, preferably 200,000 to 1,500,000.

The amount of (B) to be incorporated is, from the sensitivity and adhesion viewpoint, generally 70 to 99% by mass, preferably 80 to 99% by mass, based on the mass of the photosensitive composition.

(B) may comprise a single species or a mixture of two or more species.

The composition of the invention may contain an adhesion improving agent (C), if necessary for improving the adhesion of the composition to the glass surface. By incorporating (C), it is possible to improve the adhesion to glass. As (C), there may be mentioned silane coupling agents [e.g. amino-containing silane coupling agents such as vinyl-tris (β-methoxyethoxy)silane, N-β-(aminoethyl)-γ-aminopropylmethyldimethoxysilane, N-β-(aminoethyl)-γ-aminopropyltrimethoxysilane, N-β-(aminoethyl)-γ-aminopropyltriethoxysilane, γ-aminopropyltrimethoxysilane and γ-aminopropyltriethoxysilane; glycidyl-containing silane coupling agents such as γ-glycidoxypropyltrimethoxysilane, γ-glycidoxypropyltriethoxysilane and γ-glycidoxypropylmethyldiethoxysilane; etc.], titanium coupling agent [e.g. dihydroxybis(lactado)titanium, dialkylbis(triethanol aluminato)titanium, oxotitaniumbis (monoammonium oxalate), etc.], organic carboxylic acid compounds, organophosphorus compounds and, organophosphate compounds, among others. From the adhesion strength viewpoint, however, silane coupling agents and titanium coupling agents are preferred.

The amount of (C), if incorporated, is generally not more than 10% by mass, preferably 0.01 to 5% by mass, from the adhesion effect and resolution viewpoint, based on the mass of (B).

The composition of the present invention may contain a water-soluble solvent as a diluent. By incorporating such a diluent, it becomes possible to adjust the spreadability, storage stability, development characteristics and adhesiveness of the composition, among others.

The diluent is not particularly restricted but may be any one miscible with the respective components. Thus, for example, there may be mentioned water; alcohol solvents such as methanol, ethanol and isopropyl alcohol; glycol solvents such as methylcellosolve, ethylcellosolve, butylcellosolve, diethylene glycol monomethyl ether and diethylene glycol monoethyl ether; and amide solvents such as N-methylpyrrolidone, 2-pyrrolidone, dimethylformamide and N,N-dimethylacetamide, among others.

Preferred among them from the sensitivity and resolution viewpoint are water, alcohol solvents and glycol ether solvents, and, particularly preferred is water.

The amount of the diluent may be selected arbitrarily according to the conditions of application of the photosensitive composition, among others. Generally, however, the diluent is used preferably in an amount of 2 to 100 times, in particular 5 to 70 times, based on the mass of the water-soluble vinyl (co)polymer.

The photosensitive composition of the invention may further contain a surfactant, if necessary for improving the substrate wetting ability. The surfactant is not particularly restricted but may be any of those miscible with the respective components, such as anionic, nonionic and cationic surfactants.

Preferred among them from the stability viewpoint are nonionic surfactants (e.g. sorbitan ester-ethylene oxide adducts, alkylphenol-ethylene oxide adducts).

When a surfactant is incorporated, the amount thereof is generally not more than 5% by mass, preferably 0.05 to 3% by mass, based on the mass of (B) from the additive effect and developability viewpoint.

The photosensitive composition of the invention may further contain, as necessary, a low molecular compound having a hydroxy group(s) and/or an iodine atom(s) within the molecule and having a molecular weight of not more than 990. By incorporating such low molecular compound, it is possible to adjust the development characteristics and adhesiveness, among others, and further to improve the sensitivity.

As the hydroxy-containing low molecular compounds, there may be mentioned n-butanol, ethylene glycol, diethylene glycol, propylene glycol, 1,3-butylene glycol, 1,5-pentanediol, triethanolamine, glycerol, erythritol, pentaerythritol, sorbitol, hexitol and dipentaerythritol, among others.

As the iodine-containing low molecular compounds, there may be mentioned, for example, iodoacetic acid, 3,5-diamino-2,4,6-triiodobenzoic acid, sodium 3,5-diamino-2,4,6-triiodobenzoate, 3-amino-2,4,6-triiodobenzoic acid, sodium 3-amino-2,4,6-triiodobenzoate, 5-amino-2,4,6-triiodoisophthalic acid, sodium 5-amino-2,4,6-triiodoisophthalate, 5-amino-2,4,6-triiodoisophthalamic acid, sodium 5-amino-2,4,6-triiodoisophthalamate, 3,5-diiodosalicylic acid, sodium 3,5-diiodosalicylate, 2,3,5-triiodobenzoic acid, sodium 2,3,5-triiodobenzoate, tetraalkylammonium iodides, sodium iodide and potassium iodide.

When such hydroxy- and/or iodine-containing low molecular compound is incorporated, the amount thereof is generally 1 to 200% by mass, preferably 1 to 100% by mass, based on the mass of (B) from the additive effect and developability viewpoint.

The water-soluble photosensitive compound and water-soluble photosensitive composition of the present invention are highly useful in fine pattern forming resists, color cathode ray tube inside surface pattern forming resists, shadow mask forming etching resists, color filter black matrix forming resists, color filter pigment dispersing resists, plasma display panel patterning resists, field emission display patterning resists, fluorescent display tube patterning resists, printed circuit board soldering resists, printed circuit board etching resists, printed circuit board dry film resists, interlayer isolating materials, liquid crystal transparent conductive layer (TO) patterning resists, photosensitive printing plates, printing inks, photocuring coating compositions and the like and, in particular, they are very useful in fine pattern forming resists and color cathode ray tube-inside surface pattern forming resists (color cathode ray tube black matrix forming resists, color cathode ray tube fluorescent material patterning resists, color cathode ray tube pigment filter patterning resists, etc.).

As a specific example of the use of the photosensitive composition of the present invention, fine pattern formation is explained in the following.

The method of fine pattern formation comprises, for example, the following series of steps:

Applying the photosensitive composition of the invention to a glass substrate generally by spin coating or the like technique to a thickness of 0.1 to 2 μm;

Drying the coating using a hot plate, infrared heater, far infrared heater or the like to form a film;

Exposing the film to ultraviolet rays from a super-high pressure mercury lamp, high pressure mercury lamp, metal halide lamp or xenon lamp or the like through a photomask having a desired pattern generally at 0.5 to 100 mJ/cm$^2$; and Developing and removing the unexposed portions by washing.

When the photosensitive composition of the invention is used in color cathode ray tube black matrix formation, the resolution can further be improved since the composition has a reciprocity law failure property.

The reciprocity law failure property is the property such that a pattern of stripes or dots substantially smaller in area than the light exposure areas is formed on a glass surface in the presence of gaseous oxygen.

The filter and lens, among others, of the exposure apparatus for exposing the photosensitive composition of the invention to ultraviolet rays are preferably made of a material showing low light absorption in the vicinity of 240 to 305 nm, in particular quartz. Soda lime glass fairly absorbs ultraviolet rays not longer than 305 nm in wavelength, hence is not preferred.

BEST MODES FOR CARRYING OUT THE INVENTION

The following examples illustrate the present invention in further detail. They are, however, by no means limitative of the scope of the invention. In the following, "part(s)" means "part(s) by mass" and "%" means "% by mass".

The sensibility has various definitions, however, that is defined herein as the exposure time until the ratio (residual film ratio) of film thickness after exposure and development under a constant illumination becomes 50% relative to the initial thickness. In this case, the shorter is the exposure time, the higher is the sensibility.

EXAMPLE 1

Synthesis of disodium 4,4'-diazido-2,2'-methylenedibenzenedisulfonate (1) 3-Anilinesulfonic acid (10 g, 57.8 mmol) was dissolved in a mixed solvent composed of 4.5 g of 37% formalin (in water), 20 g of concentrated hydrochloric acid (pure substance content 35%) and 20 g of water, and the reaction was allowed to proceed at 80° C. for 5 hours. The reaction mixture was allowed to cool, then made alkaline by addition of sodium hydroxide, and poured into 500 ml of acetone, and the resulting solid precipitate was collected by filtration to give 6.7 g (16.7 mmol) of crude disodium 4,4'-diamino-2,2'-methylenedibenzenedisulfonate [yield=58%].

(2) The crude disodium 4,4'-diamino-2,2'-methylenedibenzenedisulfonate obtained in (1) (6.7 g, 16.7 mmol) was dissolved in a mixed solvent composed of 100 g of water and 5 g of concentrated hydrochloric acid (pure substance content 35%) and the solution was cooled to 0 to 5° C. To this was added an aqueous solution (5 ml) containing 1.3 g (18.4 mmol) of sodium nitrite, and the mixture was further stirred at 0 to 5° C. for 1 hour. To this was added an aqueous solution (5 ml) containing 1.1 g (16.7 mmol) of sodium azide at 0 to 5° C., and the mixture was stirred at room temperature for 5 hours. This reaction mixture was made alkaline by addition of sodium hydroxide and poured into 1,000 ml of acetone, and the resulting solid precipitate was collected by filtration and dried to give 6.1 g (12.5 mmol) of disodium 4,4'-diazido-2,2'-methylenedibenzenedisulfonate dihydrate [yield=75%].

Elemental analysis

| Calculated values: | Found values: |
| --- | --- |
| C: 31.840 | C: 31.752 |
| H: 2.467 | H: 2.448 |
| N: 17.138 | N: 17.192 |

$^1$H-NMR (ppm); 3.81 (s, 2H), 7.60–7.70 (m, 4H), 8.30 (d, 2H) Absorption maximum wavelength: 259 nm.

EXAMPLE 2

Synthesis of disodium 4,4'-diazido-3,3'-methylenedibenzenedisulfonate (1) 2-Anilinesulfonic acid (10 g, 57.8 mmol) was dissolved in a mixed solvent composed of 4.5 g of 37% formalin (in water), 20 g of concentrated hydrochloric acid (pure substance content 35%) and 20 g of water, and the reaction was allowed to proceed at 80° C. for 5 hours. The reaction mixture was allowed to cool, then made alkaline by addition of sodium hydroxide, and poured into 500 ml of acetone, and the resulting solid precipitate was collected by filtration to give 7.4 g (18.5 mmol) of crude disodium 4,4'-diamino-3,3'-methylenedibenzenedisulfonate [yield=64%].

(2) The crude disodium 4,4'-diamino-3,3'-methylenedibenzenedisulfonate obtained in (1) (7.4 g, 18.5 mmol) was dissolved in a mixed solvent composed of 100 g of water and 5 g of concentrated hydrochloric acid (pure substance content 35%) and the solution was cooled to 0 to 5° C. To this was added an aqueous solution (5 ml) containing 1.4 g (20.4 mmol) of sodium nitrite and the mixture was further stirred at 0 to 5° C. for 1 hour. To this was added an aqueous solution (5 ml) containing 1.2 g (18.5 mmol) of sodium azide at 0 to 5° C., and the mixture was stirred at room temperature for 5 hours. The reaction mixture was made alkaline by addition of sodium hydroxide and poured into 1,000 ml of acetone, and the resulting solid precipitate was collected by filtration and dried to give 6.2 g (12.6 mmol) of disodium 4,4'-diazido-3,3'-methylenedibenzenedisulfonate dihydrate [yield=68%].

Elemental analysis

| Calculated values: | Found values: |
| --- | --- |
| C: 31.840 | C: 31.892 |
| H: 2.467 | H: 2.470 |
| N: 17.138 | N: 17.089 |

$^1$H-NMR (ppm); 3.81 (s, 2H), 7.41 (m, 2H), 7.92–8.11 (m, 4H) Absorption maximum wavelength: 262 nm.

EXAMPLE 3

Synthesis of disodium 4,4'-diazido-2,2'-(1,2-ethanediylbenzene)disulfonate (1) Disodium 4,4'-diamino-2,2'-stilbenedisulfonate (20 g, 48.7 mmol) was dissolved in 150 ml of ethanol, 1.0 g of 5% palladium-carbon was added thereto, and hydrogenation was effected by stirring the mixture at room temperature in a hydrogen atmosphere at ordinary pressure. After confirmation of cessation of hydrogen absorption, the 5% palladium-carbon was filtered off, and the ethanol was distilled off under reduced pressure to give 18.4 g (44.3 mmol) of crude disodium 4,4'-diamino-2,2'-(1,2-ethanediylbenzene)disulfonate [yield=91%].

(2) The crude disodium 4,4'-diamino-2,2'-(1,2-ethanediylbenzene)disulfonate (18.4 g, 44.3 mmol) was dissolved in a mixed solvent composed of 800 g of water and 13 g of concentrated hydrochloric acid (pure substance content 35%), and the solution was cooled to 0 to 5° C. To this was added an aqueous solution (12 ml) of 3.4 g (48.7 mmol) of sodium nitrite, and the mixture was further stirred at 0 to 5° C. for 1 hour. Thereto was added an aqueous solution (12 ml) of 2.9 g (44.3 mmol) of sodium azide at 0 to 5° C., and the mixture was stirred at room temperature for 5 hours. The reaction mixture was made alkaline by addition of sodium hydroxide and then poured into 5,000 ml of acetone, and the resulting solid precipitate was collected by filtration and dried to give 15.6 g (31.0 mmol) of disodium 4,4'-diazido-2,2'-(1,2-ethanediylbenzene)disulfonate dihydrate [yield=70%].
Elemental analysis

| Calculated values: | Found values: |
|---|---|
| C: 33.337 | C: 33.319 |
| H: 2.798 | H: 2.804 |
| N: 16.661 | N: 16.642 |

$^1$H-NMR (ppm); 2.88 (s, 4H), 7.21–7.38 (m, 4H), 7.88 (d, 2H) Absorption maximum wavelength: 258 nm.

EXAMPLE 4

Synthesis of disodium 4,4'-diazido-2,2'-biphenylenedisulfonate (1) 3-Nitrobenzenesulfonic acid (10 g, 49.3 mmol) was dissolved in 40 ml of ethanol, 25 g of zinc dust was added thereto, and the mixture was heated under reflux. While continuing the refluxing, an aqueous solution of sodium hydroxide (15 g/50 ml) and 40 ml of ethanol were added in that order, and the refluxing was conducted for 2 hours. Zinc dust (5 g) was then added and the refluxing was further continued for 4 hours. Thereafter, the reaction mixture was poured into 150 ml of a 30% aqueous solution of acetic acid supplemented with 0.5 g of sodium nitrite, and the solid obtained was washed with ethanol and dried to give 7.8 g (22.7 mmol) of crude hydrazobenzene-3,3'-sulfonic acid [yield=92%].

(2) The crude hydrazobenzene-3,3'-sulfonic acid (7.8 g, 22.7 mmol) obtained in (1) was dissolved in 50 ml of ether followed by addition of 35 ml of concentrated hydrochloric acid (pure substance content 35%), and the mixture was stirred vigorously at room temperature for 1 hour. The precipitate solid was collected by filtration, washed with ether and then added to 100 ml of a 10% aqueous solution of sodium hydroxide, and the mixture was stirred at 80° C. for 1 hour. After allowing to cool, the reaction mixture was extracted with ether, and the ether was then removed to give 6.3 g (16.1 mmol) of crude disodium 4,4'-diamino-2,2'-biphenylenedisulfonate [yield=71%].

(3) The crude disodium 4,4'-diamino-2,2'-biphenylenedisulfonate (6.3 g, 16.1 mmol) obtained in (2) was dissolved in a mixed solvent composed of 100 g of water and 5 g of concentrated hydrochloric acid (pure substance content 35%), and the mixture was cooled to 0 to 5° C. To this was added an aqueous solution (5 ml) containing 1.2 g (17.7 mmol) of sodium nitrite, and the mixture was further stirred at 0 to 5° C. for 1 hour. Then, an aqueous solution (5 ml) containing 1.0 g (16.1 mmol) of sodium azide was added at 0 to 5° C. and the whole mixture was stirred at room temperature for 5 hours. This reaction mixture was made alkaline by addition of sodium hydroxide and then poured into 1,000 ml of acetone. The resulting precipitate solid was collected by filtration and dried to give 4.8 g (10.1 mmol) of disodium 4,4'-diazido-2,2'-biphenylenedisulfonate dihydrate [yield=63%].
Elemental analysis

| Calculated values: | Found values: |
|---|---|
| C: 30.257 | C: 30.271 |
| H: 2.116 | H: 2.111 |
| N: 17.642 | N: 17.621 |

$^1$H-NMR (ppm); 7.32 (m, 2H), 7.76–7.99 (m, 4H) Absorption maximum wavelength: 262 nm.

EXAMPLE 5

According to the formulation shown below, the specified components were mixed up to give a photosensitive composition (1) of the invention. The composition (1) was applied to a glass substrate to a film thickness of 0.5 μm by spin coating and then dried on a hot plate at 50° C. for 1 minute to form a coat film. Then, this film was exposed to ultraviolet rays at an exposure illuminance of 2.5 mW/cm$^2$ through a 50 μm line width photomask using a proximity exposure machine equipped with a super-high pressure mercury lamp. The proximity gap was set at 50 μm. Thereafter, development was carried out using water at ordinary temperature to thereby form a resist pattern, and the sensitivity was determined. The sensitivity was 1.0 second (luminous exposure: 2.5 mJ/cm$^2$).

Exposure to ultraviolet rays was also carried out using Sharpness Test Chart No. 1 (product of Toppan Printing Co.) as the photomask under the following conditions: exposure illuminance 2.5 mW/cm$^2$, exposure time 10 seconds (luminous. exposure 25 mJ/cm$^2$, proximity gap 50 μm. Thereafter, development was effected with water at ordinary temperature to thereby form a resist pattern, and the resolution was determined. The resolution was 5 μm.

[Formulation of photosensitive composition (1)]

| | |
|---|---|
| Aqueos solution of polyvinylformamide ("PNVF 0500", product of Mitsubishi Chemical) (solid concentration = 30%) | 10 parts |
| Photosensitive compound obtained in Example 1 | 0.3 part |
| Surfactant ("Nonipol 100", product of Sanyo Chemical Industries) | 0.03 part |
| Silane coupling agent ("KBM-603", product of Shin-Etsu Chemical)] | 0.03 part |
| Water | 100 parts |

EXAMPLE 6

A photosensitive composition (2) was prepared according to the formulation shown below. Using it, a resist pattern was formed by its application, drying, exposure and development with water at ordinary temperature and the sensitivity was measured in the same manner as in Example 5. The sensitivity was 1.5 seconds (luminous exposure: 3.8 mJ/cm$^2$).

The resolution was measured in the same manner as in Example 5 and found to be 5 μm.

[Formulation of photosensitive composition (2)]

| | |
|---|---|
| Aqueous solution of polyvinylpyrrolidone ("PVP K-90", product of ISP) (solid concentration = 10%) | 30 parts |
| Photosensitive compound obtained in Example 1 | 0.3 part |
| Surfactant ("Nonipol 100", product of Sanyo Chemical Industries) | 0.03 part |
| Silane coupling agent ("KBM-603", product of Shin-Etsu Chemical) | 0.03 part |
| Water | 80 parts |

COMPARATIVE EXAMPLE 1

A photosensitive composition for comparison (Compar. 1) was prepared according to the formulation shown below. Using it, a resist pattern was formed by its application, drying, exposure and development with water at ordinary temperature and the sensitivity was measured in the same manner as in Example 5. The sensitivity was 2.5 seconds (luminous exposure: 6.3 mJ/cm$^2$).

The resolution was measured in the same manner as in Example 5 and found to be 15 μm.

[Formulation of photosensitive composition (Compar. 1)]

| | |
|---|---|
| Aqueous solution of polyvinylpyrrolidone ("PVP K-90", product of ISP) (solid concentration = 10%) | 30 parts |
| Disodium 4,4'-diazidostilbene-2-2'-disulfonate | 0.3 part |
| Surfactant ("Nonipol 100", product of Sanyo Chemical Industries) | 0.03 part |
| Silane coupling agent ("KBM-603", product of Shin-Etsu Chemical) | 0.03 part |
| Water | 80 parts |

INDUSTRIAL APPLICABILITY

The photosensitive compound and photosensitive composition of the invention produce the following effects and have very high utility.

1) The photosensitive compound of the invention has an absorption maximum wavelength of less than 305 nm, and a photosensitive composition containing said photosensitive compound is very high in resolution, in particular in resolution in proximity exposure, hence enables formation of fine patterns with high dimension accuracy.

2) Such hazardous substances as chromium compounds are not contained, so that no equipment is required for removing such hazardous substances in waste water, hence no environmental pollution results.

What is claimed is:

1. A water-soluble photosensitive compound represented by the following general formula (1):

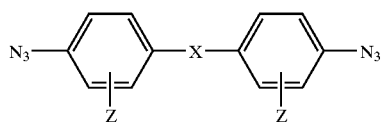

(1)

in the formula,

X represents an alkylene group containing 1 to 5 carbon atoms, —CH$_2$O—, —OCH$_2$—, —CH$_2$OCH$_2$—, —O—, —S— or —SO$_2$—, Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$, and R represents a hydrogen atom and/or an alkyl group containing 1 to 5 carbon atoms, and said alkyl group optionally having one hydroxy, ether, carbonyl, carbonyloxy or oxycarbonyl group, and the two Z groups may be the same or different or by the following general formula (2):

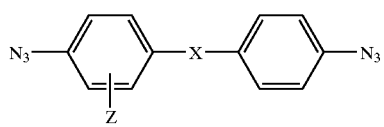

(2)

in the formula,

X represents a direct bond, an alkylene group containing 1 to 5 carbon atoms, —CH$_2$O—, —OCH$_2$—, —CH$_2$OCH$_2$—, —O—, or —SO$_2$— and Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl carbonyloxy or oxycarbonyl group, wherein a photosensitive group has an absorption maximum wavelength of not longer than 305 nm the ultraviolet absorption spectrum thereof.

2. The water-soluble photosensitive compound according to claim 1, wherein a photosensitive group has an absorption maximum wavelength, in the ultraviolet absorption spectrum, of 240 to 300 nm.

3. The water-soluble photosensitive compound according to claim 1, wherein X in general formula (1) is a methylene group or an ethylene group, and X in general formula (2) is a directed bond, a methylene group or an ethylene group.

4. The water-soluble photosensitive compound accordog to claim 1, wherein Z in general formula (1) or (2) is —SO$_3^-$.Q$^+$, said Q$^+$ being Li$^+$, Na$^+$, K$^+$ or N$^+$R$_4$, said R representing a hydrogen atom and/or an alkyl group containing 1 to 5 carbon atoms, and said alkyl group optionally having one hydroxy, ether, carbonyl, carbonyloxy or oxycarbonyl group.

5. The water-soluble photosensitive compound according to claim 1, wherein said compound is disodium 4,4'-diazido-2,2'-methylenedibenzenedisulfonate, disodium 4,4'-diazido-3,3'-methylenedibenzenedisulfonate, disodium 4,4'-diazido-2,2'-(1,2-ethanediyldibenzene)disulfonate or disodium 4,4'-diazido-3,3'-(1,2-ethanediyldibenzene)disulfonate.

6. A photosensitive compostion comprising 1 to 30% by mass of a water-soluble photosensitive compound (A) and 70 to 99% by mass of a water-soluble vinyl (co)polymer (B), wherein a photosensitive group in said (A) has an absorption maximum wavelength of not longer than 305 nm in the ultraviolet absorption spectrum thereof wherein said water-soluble photosensitive compound (A) is represented by the following general formula (1):

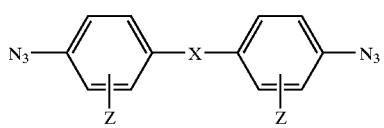

(1)

in the formula,

X represents a direct bond, an alkylene group containing 1 to 5 carbon atoms, —CH$_2$O—, —OCH$_2$—, —CH$_2$OCH$_2$—, —O—, —S— or —SO—, Z represents —SO$_3^-$.Q$^+$, —COO$^-$.Q or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl, carbonyloxy or oxycarbonyl group, and the two Z groups may be the same or different or by the following general formula (2):

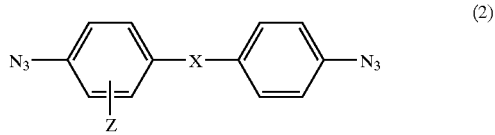

(2)

in the formula,

X represents a direct bond, an alkylene group containing 1 to 5 carbon atoms, —CH$_2$O—, —OCH$_2$—, —CH$_2$OCH$_2$—, —O—, —S— or —SO$_2$— and Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group containing 1 to 5 carbon atoms, said alkyl group optionally having one hydroxy, ether, carbonyl, carbonyloxy or oxycarbonyl group, wherein the compound of the general formula (1) is disodium 4,4'-diazido-2,2'-biphenylenedisulfonate when X in the general formula (1) represents a direct bond.

7. The photosensitive composition according to claim 6, wherein a photosensitive group of said water-soluble photosensitive compound (A) has an absorption maximum wavelength, in the ultraviolet absorption spectrum, of 240 to 300 nm.

8. The photosensitive composition according to claim 6, wherein said water-soluble photosensitive compound (A) is a water-soluble azide compound.

9. The photosensitive composition according to claim 6, wherein X in general formula (1) or (2) is a direct bond, a methylene group or an ethylene group.

10. The photosensitive composition according to claim 6, wherein Z in general formula (1) or (2) is —SO$_3^-$.Q$^+$, said Q$^+$ being Li$^+$, Na$^+$, K$^+$ or N$^+$R$_4$, R representing a hydrogen atom and/or an alkyl group containing 1 to 5 carbon atoms, and said alkyl group optionally having one hydroxy, ether, carbonyl, carbonyloxy or oxycarbonyl group.

11. The photosensitive composition according to claim 6, wherein the water-soluble vinyl (co)polymer (B) comprises at least one member selected from the group consisting of N-vinylpyrrolidone (co)polymers, N-vinylformamide (co)polymers, N-vinylacetamide (co)polymers (meth)acrylamide (co)polymers, N-C$_{1-5}$-alkyl(meth)acrylamide, N,N-di-C$_{1-5}$-alkyl(meth) acrylamide, (meth)acrylamide-diacetone(meth) acrylamide copolymers, acryloylmorpholine (co) polymers, acrylamide-2-methylpropanesulfonic acid (co)polymers, vinyl alcohol (co)polymers, sodium styrenesulfonate (co)polymers and (meth)acrylic acid (co) polymers.

12. The photosensitive composition according to claim 6 which comprises 0.01 to 10% by mass, based on the mass of said water-soluble vinyl (co)polymer (B), of an adhesion improving agent (C).

13. The photosensitive composition according to claim 6 which has a reciprocity law failure property.

14. The photosensitive composition according to claim 6 being suitable for use in color cathode ray tube inside surface pattern formation.

15. The photosensitive composition according to claim 14, wherein the inside surface pattern formation is black matrix formation.

16. The water-soluble photosensitive compound according to claim 2, wherein X in general formula (1) a methylene group or an ethylene group, and X in general formula (2) is a direct bond, a methylene group or an ethylene group.

17. The water-soluble photosensitive compound according to claim 2, wherein Z in general formula (1) or (2) is —SO$_3^-$.Q$^+$, said Q$^+$ being Li$^+$, Na$^+$, K$^+$ or N$^+$R$_4$, said R representing a hydrogen atom and/or an alkyl group containing 1 to 5 carbon atoms, and said alkyl group optionally having one hydroxy, ether, carbonyl, carbonyloxy or oxycarbonyl group.

18. The water-soluble photosensitive compound according to claim 3, wherein Z in general formula (1) or (2) is —SO$_3^-$.Q$^+$, said Q$^+$ being Li$^+$, Na$^+$, K$^+$ or N$^+$R$_4$, said R representing a hydrogen atom and/or an alkyl group containing 1 to 5 carbon atoms, and said alkyl group optionally having one hydroxy, ether, carbonyl, carbonyloxy or oxycarbonyl group.

19. The water-soluble photosensitive compound according to claim 2, wherein said compound is disodium 4,4'-diazido-2,2'-methylenedibenzenedisulfonate, disodium 4,4'-diazido-3,3'-methylenedibenzenedisulfonate, disodium 4,4'-diazido-2,2'-(1,2-ethanediyldibenzene)disulfonate or disodium 4,4'-diazido-3,3'-(1,2-ethanediyldibenzene)disulfonate.

20. A method for producing a color cathode ray tube, comprising forming a inside surface pattern of said tube by using a photosensitive composition as a resist, wherein said photosensitive composition comprises 1 to 30% by mass of a water-soluble photosensitive compound (A) and 70 to 99% by mass of a water-soluble vinyl (co)polymer (B), wherein said water-soluble photosensitive compound (A) is represented by the following general formula (1):

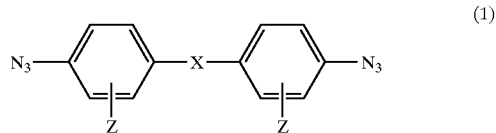

(1)

in the formula,

X represents a direct bond, an alkylene group containing 1 to 5 carbon atoms, —CH$_2$O—, —OCH$_2$—, —CH$_2$OCH$_2$—, —O—, —S— or —SO$_2$—, Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$, and R represents a hydrogen atom and/or an alkyl group containing 1 to 5 carbon atoms, and said alkyl group optionally having one hydroxy, ether, carbonyl, carbonyloxy or oxycarbonyl group, and the two Z groups may be the same or different or by the following general formula (2):

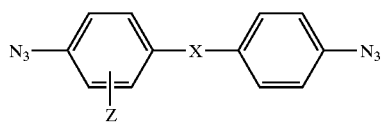

(2)

in the formula,

X represents a direct bond, an alkylene group containing 1 to 5 carbon atoms, —CH$_2$O—, —OCH$_2$—, —CH$_2$OCH$_2$—, —O—, —S— or —SO$_2$— and Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$ and R represents a hydrogen atom and/or an alkyl group contain 1 to 5 carbon atoms, said alkyl group optionally having one hydroxy, ether, carbonyl, carbonyloxy or oxycarbonyl group, wherein a photosensitive group in said compound (A) has an absorption maximum wavelength of not longer than 305 nm in the ultraviolet absorption spectrum thereof.

21. A color cathode ray tube obtained by forming a inside surface pattern of said tube by using a photosensitive composition as a resist, wherein said photosensitive composition comprises 1 to 30% by mass of a water-soluble photosensitive compound (A) and 70 to 99% by mass of a water-soluble vinyl (co)polymer (B), wherein said water-soluble photosensitive compound (A) is represented by the following general formula (1):

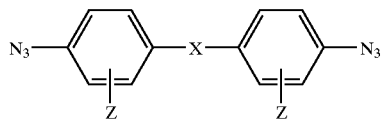

(1)

in the formula,

X represents a direct bond, an alkylene group containing 1 to 5 carbon atoms, —CH$_2$O—, —OCH$_2$—, —CH$_2$OCH$_2$—, —O—, —S— or —SO$_2$—, Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$, and R a hydrogen atom and/or an alkyl group containing 1 to 5 carbon atoms, and said alkyl group optionally having one hydroxy, ether, carbonyl, carbonyloxy or oxycarbonyl group, and the two Z groups may be the same or different or by the following general formula (2):

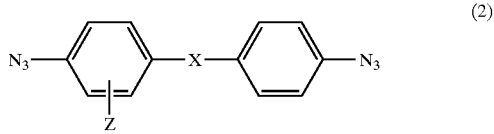

(2)

in the formula,

X represents a direct bond, an alkylene group containing 1 to 5 carbon atoms, —CH$_2$O—, —OCH$_2$—, —CH$_2$OCH$_2$—, —O—, —S— or —SO$_2$—, Z represents —SO$_3^-$.Q$^+$, —COO$^-$.Q$^+$ or —SO$_2$NR$_2$, in which Q$^+$ represents Li$^+$, Na$^+$, K$^+$ or N$^+$R$_4$, and R a hydrogen atom and/or an alkyl group containing 1 to 5 carbon atoms, and said alkyl group optionally having one hydroxy, ether, carbonyl, carbonyloxy or oxycarbonyl group, wherein a photosensitive group in said compound (A) has an absorption maximum wavelength of not longer than 305 nm in the ultraviolet absorption spectrum thereof.

* * * * *